US010098296B2

(12) United States Patent
Garcia-Andres et al.

(10) Patent No.: US 10,098,296 B2
(45) Date of Patent: Oct. 16, 2018

(54) MELON PLANTS WITH IMPROVED DISEASE TOLERANCE

(71) Applicant: Seminis Vegetable Seeds, Inc., St. Louis, MO (US)

(72) Inventors: Susana Garcia-Andres, St. Louis, MO (US); Eleni Bachlava, Fairfield, CA (US); Eva King-Fan Chan, Rosebery (AU); Tarek Joobeur, Sacramento, CA (US); Joseph J. King, Davis, CA (US); Petrus J. Kraakman, Aguadulce (ES); Subash Krishnamurthy, St. Peters, MO (US); Jeffrey M. Mills, Woodland, CA (US); Jeroen de Vries, Bergschenhoek (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 75 days.

(21) Appl. No.: 14/880,050

(22) Filed: Oct. 9, 2015

(65) Prior Publication Data

US 2016/0102318 A1 Apr. 14, 2016

Related U.S. Application Data

(63) Continuation of application No. 14/559,858, filed on Dec. 3, 2014, now Pat. No. 9,578,824.

(60) Provisional application No. 62/062,680, filed on Oct. 10, 2014, provisional application No. 62/062,491, filed on Oct. 10, 2014, provisional application No. 62/062,501, filed on Oct. 10, 2014.

(51) Int. Cl.
*A01H 5/08* (2018.01)
*A01H 1/04* (2006.01)
*C12N 15/82* (2006.01)

(52) U.S. Cl.
CPC ............... *A01H 5/08* (2013.01); *A01H 1/04* (2013.01); *C12N 15/8283* (2013.01)

(58) Field of Classification Search
None
See application file for complete search history.

(56) References Cited

U.S. PATENT DOCUMENTS 8,669,413 B2 * 3/2014 Superak ............... A01H 3/00
800/265
2016/0100537 A1 4/2016 Kraakman
2016/0100539 A1 4/2016 Kraakman

FOREIGN PATENT DOCUMENTS

EP 1800535 6/2007
WO WO 2004/001046 12/2003

OTHER PUBLICATIONS

U.S. Appl. No. 14/880,058, filed Oct. 9, 2015, Kraakman.
U.S. Appl. No. 14/559,858, filed Dec. 3, 2014, Kraakman.
USPTO: Notice of Allowance and Fees Due regarding U.S. Appl. No. 14/880,058, dated Jul. 28, 2016.
USPTO: Notice of Allowance and Fees Due regarding U.S. Appl. No. 14/559,858, dated Jul. 25, 2016.
USPTO: Non-Final Office Action regarding U.S. Appl. No. 14/559,858, dated Feb. 25, 2016.
European Extended Search Report regarding European Application No. EP 15189209, dated Feb. 15, 2016.
Lopez-Sese et al., "Resistance to Cucurbit Yellowing Stunting Disorder Virus (CYSDV) in *Cucumis melo* L.," Hort Science 35(1):110-113, 2000.
Park et al., "Detection of Loci for Cucurbit Yellow Stunting Disorder Virus Resistance in *Cucumis mello* L.," *ACTA Horticulturae* 763:207-214, 2007.
Sinclair, "Screening for Resistance to Cucurbit Yellow Stunting Disorder Virus, Gummy Stem Blight, and Monosporascus Root Rot and Detection of RAPD Markers Associated with QTL for Soluble Solids, Sugars, and Vitamin C in Melon (*Cucumis Melo* L.)," Theseis, Texas A&M University, Dec. 2003.
USPTO: Non-Final Office Action regarding U.S. Appl. No. 14/880,058, dated Jul. 28, 2016.
Response to Non-Final Office Action regarding U.S. Appl. No. 14/559,858, dated Jul. 25, 2016.

* cited by examiner

*Primary Examiner* — Brent T Page
(74) *Attorney, Agent, or Firm* — Dentons US LLP; Matthew Madsen, Esq.

(57) ABSTRACT

The present disclosure provides melon plants exhibiting tolerance to cucurbit yellow stunt disorder virus (CYSDV) and lacking negative traits associated with CYSDV tolerance such as increased fruit size and reduced fruit set. Such plants may comprise novel introgressed genomic regions associated with disease tolerance. In certain aspects, compositions, including novel polymorphic markers and methods for producing, breeding, identifying, and selecting plants or germplasm with a disease tolerance phenotype are provided.

25 Claims, 6 Drawing Sheets

Specification includes a Sequence Listing.

FIG. 1

| entry | scoring 1 LSMean | scoring 1 StdErr | scoring 2 LSMean | scoring 2 StdErr | scoring 2 LSD |
|---|---|---|---|---|---|
| A1 | 1.39 | 0.36 | 2.00 | 0.38 | F |
| A2 | 1.34 | 0.45 | 1.86 | 0.48 | F |
| B1 | 4.78 | 0.45 | 6.99 | 0.46 | B |
| B2 | 5.15 | 0.52 | 9.27 | 0.53 | A |
| C1 | 6.03 | 0.39 | 6.30 | 0.42 | BCD |
| C2 | 4.86 | 0.38 | 5.73 | 0.41 | DE |
| F | 1.15 | 0.45 | 1.66 | 0.50 | F |
| H | 1.10 | 0.39 | 2.15 | 0.42 | F |
| I | 1.26 | 0.38 | 2.15 | 0.44 | F |
| L | 4.47 | 0.37 | 6.05 | 0.40 | BCD |
| M | 4.80 | 0.40 | 6.17 | 0.43 | BCD |
| NO | 4.35 | 0.42 | 6.94 | 0.44 | B |
| T | 4.27 | 0.38 | 5.76 | 0.40 | CDE |
| V | 5.04 | 0.39 | 7.01 | 0.42 | B |
| W | 5.22 | 0.45 | 7.17 | 0.50 | B |
| Y | 2.77 | 0.49 | 6.98 | 0.56 | BC |
| Z | 4.57 | 0.42 | 4.98 | 0.46 | E |
| AA | 3.85 | 0.47 | 5.52 | 0.50 | DE |
| ABAC | 1.54 | 0.47 | 6.48 | 0.53 | BCD |

| chr | | 9 | 9 | 9 | 9 | 9 | 9 | 9 | 9 |
|---|---|---|---|---|---|---|---|---|---|
| cM | | 146.9 | 148.4 | 149.2 | 153.0 | 154.0 | 157.9 | 162.4 | 168.0 |
| | | NU0220874 | NU0218332 | NU0218606 | NU0219432 | NU0220587 | NU0243519 | NU0220669 | NU0218088 |
| DP | | AA | AA | AA | CC | CC | GG | CC | CC |
| DP | | AA | AA | AA | CC | CC | GG | CC | CC |
| RP | | TT | CC | GG | TT | GG | AA | TT | TT |
| RP | | TT | CC | GG | TT | GG | AA | TT | TT |
| | | AT | AC | AG | TC | CG | AG | TC | TC |
| | | AT | AC | AG | TC | CG | AG | TC | TC |
| | | AA | AA | AA | TC | CG | AG | TC | TC |
| | | AA | AA | AA | CC | CC | GG | CC | CC |
| | | AT | AC | AG | TC | CG | AG | TC | TC |
| | | AT | AC | AG | CC | CG | GG | CC | CC |
| | | AT | AC | AG | TC | CC | AG | CC | CC |
| | | AT | AC | AG | CC | CC | GG | CC | CC |
| | | TT | CC | GG | TC | CG | AG | TC | TC |
| | | TT | CC | GG | TT | GG | AG | TC | TC |
| | | TT | CC | GG | TT | GG | AA | TC | TT |
| | | AT | AC | AG | TC | CG | AG | TT | TT |
| | | AT | AC | AG | TC | CG | AG | TT | TT |
| | | AT | AC | AG | TT | GG | AA | TT | TT |

FIG. 2

| Entry | LSM | L_95% | U_95% | MSG | 9<br>146.9<br>NU0220874 | 9<br>149.2<br>NU0218606 | 9<br>151.6<br>NU0219208 | 9<br>153.0<br>NU0219432 | 9<br>154.0<br>NU0220587 | 9<br>157.9<br>NU0243519 | 9<br>162.4<br>NU0220669 | 9<br>168.0<br>NU0218088 |
|---|---|---|---|---|---|---|---|---|---|---|---|---|
| 3 | 1.00 | -0.35 | 2.35 | C | AA | AA | AA | CC | CC | GG | CC | CC |
| 9 | 1.00 | -0.35 | 2.35 | C | AA | AA | AA | CC | CC | GG | TT | CC |
| 11 | 7.08 | 5.74 | 8.43 | A | TT | GG | GG | TT | GG | AA | CC | TT |
| 7 | 6.58 | 5.24 | 7.93 | A | TT | GG | GG | TT | GG | GG | CC | TT |
| 5 | 8.32 | 6.75 | 9.90 | A | TT | GG | GG | TT | CC | GG | CC | CC |
| 6 | 3.97 | 2.62 | 5.31 | B | TT | GG | GG | CC | CC | GG | CC | CC |
| 2 | 4.58 | 3.24 | 5.93 | B | AA | AA | AA | CC | CC | GG | TT | TT |
| 10 | 1.17 | -0.18 | 2.51 | C | AA | AA | AA | CC | CC | AA | TT | TT |
| 8 | 0.96 | -0.61 | 2.54 | C | AA | AA | AA | CC | GG | AA | TT | TT |
| 4 | 1.00 | -0.35 | 2.35 | C | AA | AA | AA | TT | GG | AA | TT | TT |
| 1 | 1.00 | -0.35 | 2.35 | C | AA | AA | AA | TT | GG | AA | TT | TT |

| | | | | | | | | | | SGR gene | | | | | |
|---|---|---|---|---|---|---|---|---|---|---|---|---|---|---|---|
| | generation | %RP | Chr | NU0220874 | NCMEL008710044 | NU0218606 | NCMEL008710095 | NCMEL008710150 | NCMEL008710179 | NCMEL008710187 | NCMEL009102569 | NCMEL008710191 | NU0219432 | NU0220587 | NCMEL008710520 | NCMEL008710595 |
| | | | cM (v2.2.2) | 146.91 | 147.89 | 149.19 | 148.65 | 149.55 | 149.81 | 149.93 | 149.97 | 150.70 | 152.96 | 154.04 | 155.47 | 156.52 |
| | | | | 9 | 9 | 9 | 9 | 9 | 9 | 9 | 9 | 9 | 9 | 9 | 9 | 9 |
| GALZA13-0008AN | BC2F5 | 87.81% | | TT | CC | GG | CC | AA | GG | CC | TT | CC | TT | GG | AA | AA |
| WSHZA13-0009AN | BC2F4 | 87.11% | | TT | CC | GG | CC | AA | GG | CC | TT | CC | TT | GG | AA | AA |

SEQUENCE LISTING

```
<160> NUMBER OF SEQ ID NOS: 32

<210> SEQ ID NO 1
<211> LENGTH: 18
<212> TYPE: DNA
<213> ORGANISM: Artificial Sequence
<220> FEATURE:
<223> OTHER INFORMATION: Probe

<400> SEQUENCE: 1
caatctcagc atatagac                                                 18

<210> SEQ ID NO 2
<211> LENGTH: 16
<212> TYPE: DNA
<213> ORGANISM: Artificial Sequence
<220> FEATURE:
<223> OTHER INFORMATION: Probe

<400> SEQUENCE: 2
atctcagcaa atagac                                                   16

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
```
agaagcaaag aagaaatata caaatgaaaa cgtt                                    34

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
taacctatat tcatagaatg gtgttttaat taaat                                   35

<210> SEQ ID NO 5
<211> LENGTH: 18
<212> TYPE: DNA
<213> ORGANISM: Artificial Sequence
<220> FEATURE:
<223> OTHER INFORMATION: Probe

<400> SEQUENCE: 5
tgattctgcc tattttct                                                      18

<210> SEQ ID NO 6
<211> LENGTH: 16
<212> TYPE: DNA
<213> ORGANISM: Artificial Sequence
<220> FEATURE:
<223> OTHER INFORMATION: Probe

<400> SEQUENCE: 6
attctgcctg ttttct                                                        16

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
ccaaacgcaa aactaagatg gactac                                             26

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gagtctttca tcaatctcca tgggt                                              25

<210> SEQ ID NO 9
<211> LENGTH: 17
<212> TYPE: DNA
<213> ORGANISM: Artificial Sequence
<220> FEATURE:
<223> OTHER INFORMATION: Probe

<400> SEQUENCE: 9
catttgctgg acagcct                                                       17

<210> SEQ ID NO 10
<211> LENGTH: 17
<212> TYPE: DNA

```
<213> ORGANISM: Artificial Sequence
<220> FEATURE:
<223> OTHER INFORMATION: Probe

<400> SEQUENCE: 10
catttgctgg ccagcct                                                    17

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
cctcccccat tattcaatct ccttt                                           25

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
cactggtgga agagacgatg tc                                              22

<210> SEQ ID NO 13
<211> LENGTH: 17
<212> TYPE: DNA
<213> ORGANISM: Artificial Sequence
<220> FEATURE:
<223> OTHER INFORMATION: Probe

<400> SEQUENCE: 13
attagaacca gaatctg                                                    17

<210> SEQ ID NO 14
<211> LENGTH: 16
<212> TYPE: DNA
<213> ORGANISM: Artificial Sequence
<220> FEATURE:
<223> OTHER INFORMATION: Probe

<400> SEQUENCE: 14
ttagaaccgg aatctg                                                     16

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
gacgatgcaa caacattatg gtgat                                           25

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
atcaagcaca gcaaagagtt                                                 20
```

```
<210> SEQ ID NO 17
<211> LENGTH: 16
<212> TYPE: DNA
<213> ORGANISM: Artificial Sequence
<220> FEATURE:
<223> OTHER INFORMATION: Probe

<400> SEQUENCE: 17
cgtccatgga gatgtg                                                        16

<210> SEQ ID NO 18
<211> LENGTH: 16
<212> TYPE: DNA
<213> ORGANISM: Artificial Sequence
<220> FEATURE:
<223> OTHER INFORMATION: Probe

<400> SEQUENCE: 18
cgtccatgga gttgtg                                                        16

<210> SEQ ID NO 19
<211> LENGTH: 35
<212> TYPE: DNA
<213> ORGANISM: Artificial Sequence
<220> FEATURE:
<223> OTHER INFORMATION: Primer

<400> SEQUENCE: 19
aaaaaaataa aaataaaaca ggtgctgaat gcttt                                   35

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
cctcttgtag ctctgggtaa ttctt                                              25

<210> SEQ ID NO 21
<211> LENGTH: 19
<212> TYPE: DNA
<213> ORGANISM: Artificial Sequence
<220> FEATURE:
<223> OTHER INFORMATION: Probe

<400> SEQUENCE: 21
cattgagatg gtagttcaa                                                     19

<210> SEQ ID NO 22
<211> LENGTH: 18
<212> TYPE: DNA
<213> ORGANISM: Artificial Sequence
<220> FEATURE:
<223> OTHER INFORMATION: Probe

<400> SEQUENCE: 22
attgagatgg tcgttcaa                                                      18

<210> SEQ ID NO 23
<211> LENGTH: 25
<212> TYPE: DNA
<213> ORGANISM: Artificial Sequence
<220> FEATURE:
```

```
<223> OTHER INFORMATION: Primer

<400> SEQUENCE: 23
ctggcatata tgctgtttgg tttca                                          25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
tgcatggaga ttgagacaag tcttg                                          25

<210> SEQ ID NO 25
<211> LENGTH: 19
<212> TYPE: DNA
<213> ORGANISM: Artificial Sequence
<220> FEATURE:
<223> OTHER INFORMATION: Probe

<400> SEQUENCE: 25
cacgatagta aaggttttc                                                 19

<210> SEQ ID NO 26
<211> LENGTH: 19
<212> TYPE: DNA
<213> ORGANISM: Artificial Sequence
<220> FEATURE:
<223> OTHER INFORMATION: Probe

<400> SEQUENCE: 26
cacgatagta aaagttttc                                                 19

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
gactctctcg cttatctatg ctagga                                         26

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
ggatgaaaat tgttctaatc taggttgca                                      29

<210> SEQ ID NO 29
<211> LENGTH: 16
<212> TYPE: DNA
<213> ORGANISM: Artificial Sequence
<220> FEATURE:
<223> OTHER INFORMATION: Probe

<400> SEQUENCE: 29
cccgagtcta gaaaag                                                    16
```

```
<210> SEQ ID NO 30
<211> LENGTH: 14
<212> TYPE: DNA
<213> ORGANISM: Artificial Sequence
<220> FEATURE:
<223> OTHER INFORMATION: Probe

<400> SEQUENCE: 30
cgagtccaga aaag                                                           14

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
gttctcttat tctcataagg catatgtaag gt                                       32

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
ggaaggaaaa ccctcctcta aagatc                                              26
```

MELON PLANTS WITH IMPROVED DISEASE TOLERANCE

CROSS-REFERENCE TO RELATED APPLICATIONS

This application claims the priority of U.S. Provisional Appl. Ser. No. 62/062,680, filed Oct. 10, 2014, and U.S. Provisional Appl. Ser. No. 62/062,491, filed Oct. 10, 2014. This application is also a continuation of U.S. application Ser. No. 14/559,858, filed Dec. 3, 2014, which claims the priority of U.S. Provisional Appl. Ser. No. 62/062,501, filed Oct. 10, 2014. The entire disclosure of each of the foregoing applications is specifically incorporated herein by reference in its entirety.

FIELD OF THE INVENTION

The present invention relates to the field of agriculture and more specifically to methods and compositions for producing melon plants exhibiting improved disease tolerance and plant vigor.

INCORPORATION OF SEQUENCE LISTING

The sequence listing that is contained in the file named "SEMB021USP1_ST25.txt," which is 5.76 kilobytes as measured in Microsoft Windows operating system and was created on Oct. 9, 2014, is filed electronically herewith and incorporated herein by reference.

BACKGROUND OF THE INVENTION

Disease tolerance is an important trait in agriculture, particularly for the production of food crops. Although disease tolerance alleles have been identified in uncultivated melon lines, efforts to introduce these alleles into cultivated lines have been hindered by the introduction of deleterious traits together with the tolerance alleles. The use of marker-assisted selection (MAS) in plant breeding methods has made it possible to select plants based on genetic markers linked to traits of interest such as disease tolerance. However, accurate markers for identifying or tracking desirable traits in plants are frequently unavailable even if a gene associated with the trait has been characterized. These difficulties are further complicated by factors such as polygenic or quantitative inheritance, and an often incomplete understanding of the genetic background underlying expression of a desired phenotype. Therefore, in the absence of accurate and validated markers for use in MAS, it may not be feasible to produce new plant lines exhibiting certain disease tolerance phenotypes.

SUMMARY OF THE INVENTION

In one aspect, the invention provides a melon plant of a cultivated melon variety comprising a recombinant introgression on chromosome 9 from a donor melon plant having tolerance to cucurbit yellow stunt disorder virus (CYSDV), wherein said recombinant introgression comprises a first allele conferring improved tolerance to cucurbit yellow stunt disorder virus relative to a plant lacking said first allele, and wherein said plant is homozygous for said recombinant introgression. In some embodiments, said recombinant introgression is within a genomic segment flanked by marker locus NU0218332 and marker locus NU0219432. In other embodiments, said recombinant introgression is located between approximately 148.44 cM and 153.0 cM on chromosome 9.

In another aspect, the invention provides a melon plant of a cultivated melon variety comprising a recombinant introgression on chromosome 9 from a donor melon plant having tolerance to cucurbit yellow stunt disorder virus, wherein said recombinant introgression comprises a first allele conferring improved tolerance to cucurbit yellow stunt disorder virus relative to a plant lacking said first allele, and wherein said recombinant introgression lacks a second allele genetically linked to said first allele and conferring reduced fruit set or fruit yield compared to a plant lacking said second allele. In some embodiments, said plant is heterozygous or homozygous for said recombinant introgression. In further embodiments, said recombinant introgression is within a genomic segment flanked by marker locus NCMEL008710187 and marker locus NCMEL008710191. In yet further embodiments, said recombinant introgression is within a genomic segment flanked by marker locus NCMEL008710187 and marker locus NCMEL009432571. In other embodiments, said recombinant introgression comprises marker locus NCMEL009102569. In further embodiments, said recombinant introgression is located between approximately 149.93 cM and 150.7 cM on chromosome 9. In yet further embodiments, said recombinant introgression is located between approximately 149.93 cM and 150.36 cM on chromosome 9. In other embodiments, said plant comprises DNA from said donor plant at marker locus NCMEL009102569 and recipient DNA at marker locus NCMEL008710191. The invention further provides a plant part comprising the recombined introgression provided herein, such as a cell, a seed, a root, a stem, a leaf, a fruit, a flower, or pollen.

In another aspect, the invention provides methods for producing a melon plant with improved tolerance to cucurbit yellow stunt disorder virus comprising: a) crossing the melon plant comprising a recombined introgression provided herein with itself or with a second melon plant of a different genotype to produce one or more progeny plants; and b) selecting a progeny plant comprising said recombinant introgression. In some embodiments, selecting said progeny plant comprises identifying a progeny plant that: (1) comprises donor DNA at a locus genetically linked to said first allele and/or lacks an allele present at the corresponding locus in said melon plant; and (2) lacks donor DNA at a locus genetically linked to said second allele that confers increased fruit size or reduced fruit set, and/or comprises an allele present at the corresponding locus in said melon plant. In other embodiments, selecting said progeny plant comprises marker-assisted selection (MAS). In certain embodiments, marker-assisted selection (MAS) comprises detecting at least one allele at a marker locus selected from the group consisting of: NU0220874, NU0219432, NU0218332, NU0243519, NCMEL009102569, NCMEL008710187, NCMEL008710191, and NCMEL009432571. In further embodiments, marker-assisted selection (MAS) comprises detecting at least one allele at a marker locus selected from the group consisting of: NCMEL009102569, NCMEL008710187, NCMEL008710191, and NCMEL009432571. In yet further embodiments, marker-assisted selection (MAS) comprises detecting at least one allele at a marker locus selected from the group consisting of: NCMEL009102569. In some embodiments, said progeny plant is an F2-F6 progeny plant. In other embodiments, producing said progeny plant comprises backcrossing. In yet other embodiments, backcrossing comprises from 2-7 generations of backcrossing.

In another aspect, the invention provides methods for obtaining a melon plant exhibiting improved tolerance to cucurbit yellow stunt disorder virus comprising: a) obtaining a melon plant heterozygous for a first allele that confers tolerance to cucurbit yellow stunt disorder virus and that is genetically linked in the plant to a second allele that confers increased fruit size or reduced fruit set; (b) obtaining progeny of the plant; and (c) selecting at least a first progeny plant in which recombination has occurred such that the progeny comprises said first allele that confers tolerance to cucurbit yellow stunt disorder virus but not said second allele that confers increased fruit size or reduced fruit set; wherein selecting said first progeny plant comprises detecting at least one allele at a locus selected from the group consisting of: NU0220874, NU0219432, NU0218332, NU0243519, NCMEL009102569, NCMEL008710187, NCMEL008710191, and NCMEL009432571. In some embodiments, said progeny plant is an F2-F6 progeny plant. In other embodiments, said progeny plant comprises backcrossing. In yet other embodiments, backcrossing comprises from 2-7 generations of backcrossing. In some further embodiments, the invention provides a plant produced by the methods provided herein or a part of said plant, such as a cell, a seed, a root, a stem, a leaf, a fruit, a flower, or pollen.

In still yet another aspect, provided herein is a melon plant of a cultivated melon variety comprising a recombinant introgression on chromosome 9 from a donor melon plant having tolerance to cucurbit yellow stunt disorder virus, wherein the recombinant introgression comprises a first allele conferring improved tolerance to cucurbit yellow stunt disorder virus relative to a plant lacking said first allele, and wherein the recombinant introgression is obtainable by a method of the invention. In one embodiment, the recombinant introgression is obtainable by crossing with a melon plant selected from the group of plants consisting of melon hybrid SV5133MG, melon inbred GALHK12-0024MO, melon inbred GALHK12-0044AN, melon hybrid SV5845MP, melon inbred SPAHK11-0054AN and melon inbred SPAHK11-0072AN; wherein a representative sample of seed of said plants has been deposited under ATCC Accession Numbers PTA-121630, PTA-121632, PTA-121633, PTA-121629, PTA-121626, and PTA-121627, respectively. In specific embodiments, the recombinant introgression is obtainable by crossing said plant with itself or a second plant, followed by at least about 2-10 or more generations of crossing and selection of a progeny comprising the recombinant introgression. In other embodiments, the introgression is defined as being of a reduced size relative to the recombinant introgression on chromosome 9 contained in melon hybrid SV5133MG, melon inbred GALHK12-0024MO, melon inbred GALHK12-0044AN, melon hybrid SV5845MP, melon inbred SPAHK11-0054AN or melon inbred SPAHK11-0072AN. The crossing may comprise, for example, selfing or outcrossing. Selection may be carried out at one or more generations to obtain a plant comprising the recombinant introgression. Selection may comprise phenotypic selection as described herein, and may comprise, for example, marker assisted selection employing any of the genetic markers described herein or genetic markers genetically linked thereto. In a further embodiment, selection comprises detection of markers NU0218332 or NU0243519, or any markers or sets of markers that lie between them.

BRIEF DESCRIPTION OF THE DRAWINGS

FIG. 1: Shows a fine-mapping trial of CYSDV QTL with genotypic and phenotypic data. Phenotypes are shown as least square means and standard errors for two scoring dates. The mean separation grouping is shown on the right for phenotypes of the second scoring date only. Markers and their location on consensus map v. 2.2.2 (cM) are shown together with the genotypic data of controls and recombinant entries.

FIG. 2: Shows least square mean estimates (LSM), lower and upper 95% confidence intervals (L_95% and U_95%) of these estimates, and mean separation groupings (MSG) for CYSDV disease scores in a fine-mapping trial. Genotypic data (donor and recurrent parent introgressions) for each entry and the genetic position of markers genotyped in the QTL region on chromosome 9 (cM) are shown.

FIG. 3: Shows disease phenotypes and donor introgressions of BC2-derived lines carrying recombination events near the SGR gene. CYSDV was evaluated on a 1-9 scale and is reported as least square means (R: Resistant/Tolerant; S: Susceptible; IR: Intermediate Resistant/Tolerant).

FIG. 6: Shows haplotypes of coded lines at the CYSDV QTL region. The GAL-188-CYSDV-DONOR allele introgression can be tracked using the marker NCMEL009102569. The surrounding region (in white) represents the recurrent parent background of GA35PMT or WSH-39-1067-AN.

DETAILED DESCRIPTION

Figure 4:
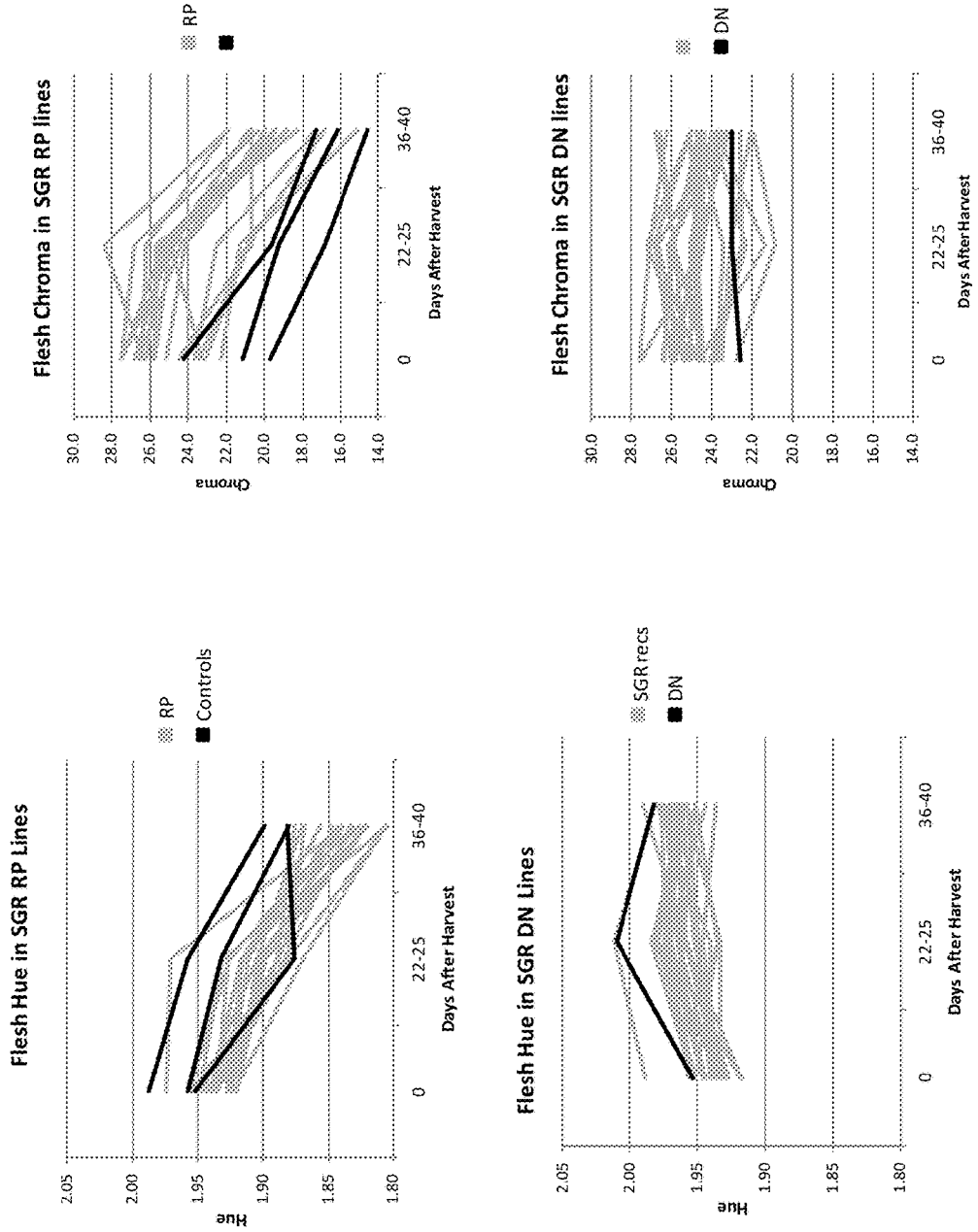
FIG. 4: Shows the change in chroma and hue of melon fruit flesh from field harvest to 40 days after cold storage. Lines carrying the donor allele at the identified CYSDV QTL interval (SGR recs), which showed no significant change in chroma or hue after cold storage, are shown on the bottom panels. Lines carrying the Galia (GAL) recurrent parent alleles at the identified CYSDV QTL interval (RP), for which chroma and hue decreased significantly after 36-40 days of cold storage, are shown on the top panels. DN: donor inbred control; Controls: GAL inbred RP and three GAL hybrids used as color controls.

Cucurbit yellow stunt disorder virus (CYSDV) is a plant pathogenic virus which is responsible for severe reduction in fruit quality in melon plants. Melon lines exhibiting tolerance to CYSDV are known, and intensive efforts have been made to introgress CYSDV tolerance alleles from these lines into other cultivated melon lines. However, these efforts have been of limited success because introgressed disease tolerance alleles have to date been associated with undesirable agronomic traits, such as low fruit set and decreased yield. Unacceptable fruit quality and yield loss due to CYSDV in melon plants therefore remains a significant problem due to the lack of a resistance trait capable of conferring CYSDV tolerance without an unacceptable level of impact on performance characteristics.

Tolerance to CYSDV has thus conventionally been obtained through introgressions which are associated with reduced fruit set and low yield in melon plants. Efforts to reduce the incidence or severity of undesirable traits in melon plants comprising CYSDV tolerance introgressions have been significantly hindered by an incomplete understanding of the genetic factors controlling CYSDV tolerance. In particular, markers and assays that accurately correlate genotype with disease tolerance and fruit yield phenotypes over a variety of melon types have previously been unavailable.

For the first time, the invention surprisingly has provided recombined introgressions of CYSDV tolerance alleles capable of use in cultivated melon lines without the deleterious traits that have previously been associated with CYSDV tolerance. The novel recombined introgressions provided by the invention result in plants which maintain plant vigor despite the presence of CYSDV, and which do not exhibit decreased yield compared with plants not comprising the recombined introgressions. The invention therefore represents a significant advance in the art. By further providing novel, accurate markers for tracking the introgressed alleles during plant breeding, the invention permits introgression of the disease tolerance alleles into any desired melon genotype.

Despite the obstacles that have previously existed to the successful use of CYSDV tolerance alleles in elite cultivated melon lines, the present inventors were thus surprisingly able to produce novel introgressions which confer tolerance to CYSDV without the deleterious traits previously associated with disease tolerance introgressions. In some embodiments, such introgressions are defined as located between approximately 148.44 cM and 153.0 cM on melon chromosome 9 on consensus map v. 2.2.2. In other embodiments, the invention provides plants comprising introgressions located between approximately 149.93 cM and 150.7 cM on chromosome 9, or between approximately 149.93 cM and 150.36 cM on chromosome 9. These novel introgressions provide robust tolerance to CYSDV, while avoiding the reduction in performance characteristics associated with conventional introgressions.

The invention further provides introgressions conferring CYSDV tolerance which can be deployed homozygously without detrimental reduction in yield or other unacceptable traits. The CYSDV tolerance alleles previously created have conventionally been deployed heterozygously in an effort to mask the deleterious traits observed with conventional introgressions. However, contrary to need for heterozygous deployment of CYSDV tolerance alleles to avoid associated negative traits, the present inventors surprisingly found that recombined CYSDV tolerance alleles could be generated without the deleterious characteristics, and therefore can be deployed homozygously without unacceptable reduction in yield. Such homozygous deployment further improves the disease tolerance phenotype therefrom as the result of having two copies of the disease tolerance allele instead of one. In other embodiments, the invention provides recombined introgressions which can be deployed heterozygously or homozygously without a reduction in fruit set or fruit yield. The novel, recombined introgressions of the present invention therefore provide significant advantages over existing technology.

Figure 3:
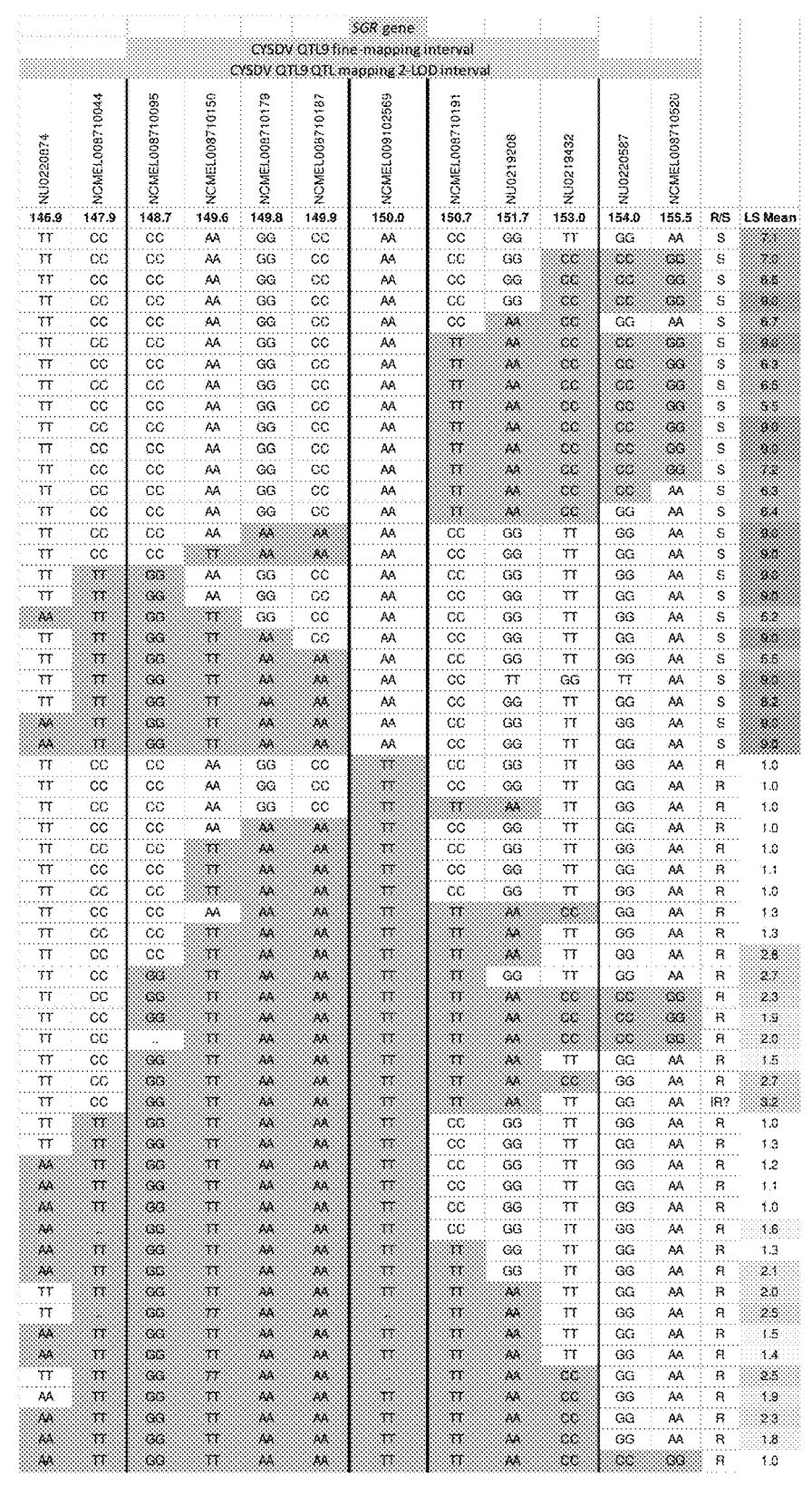

The present invention further provides novel trait-linked markers which can be used to produce plants comprising novel recombined introgressions on chromosome 9 conferring CYSDV tolerance as described herein. In particular embodiments, the invention provides the markers shown in FIGS. 1-3 and 5-7. Other embodiments of the invention provide markers NU0220874, NU0219432, NU0218332, NU0243519, NCMEL009102569, NCMEL008710187, NCMEL008710191, and NCMEL009432571, which have been shown to be genetically linked to CYSDV tolerance in plants.

The novel markers provided herein can be used to identify and track introgressions conferring tolerance to CYSDV without the deleterious traits previously associated with CYSDV tolerance alleles. In some embodiments, the present invention provides plants comprising introgressed DNA within a genomic segment flanked by marker locus NU0218332 and marker locus NU0219432, or within a genomic segment flanked by marker locus NCMEL008710187 and marker locus NCMEL008710191, or within a genomic segment flanked by marker locus NCMEL008710187 and marker locus NCMEL009432571, which exhibit CYSDV tolerance without reduction in yield. In further embodiments, the present invention provides plants comprising introgressed DNA at marker locus NCMEL009102569, which exhibit CYSDV tolerance without reduction in yield.

Because genetically diverse plant lines can be difficult to cross, the introgression of CYSDV tolerance alleles into cultivated lines using conventional breeding methods could require prohibitively large segregating populations for progeny screens with an uncertain outcome. Marker-assisted selection (MAS) is therefore essential for the effective introgression of CYSDV tolerance alleles into elite cultivars. However, previously known markers for CYSDV tolerance have failed to discriminate between donor DNA conferring disease tolerance and donor DNA conferring deleterious traits. This has been further complicated by the previous inability to resolve the specific regions associated with disease tolerance. For the first time, the present invention enables effective MAS by providing improved and validated markers for detecting genotypes associated with disease tolerance without the need to grow large populations of plants to maturity in order to observe the phenotype.

The invention further identifies a novel QTL on chromosome 9 conferring tolerance to CYSDV, as well as nucleic acid sequences and genetic markers associated with the QTL. The use of the novel markers provided herein for selection of plants having favorable alleles within or genetically linked to the newly identified QTL intervals allows for the development of plants exhibiting tolerance to CYSDV and also having acceptable yield. In some embodiments, the invention therefore provides methods of producing plants having tolerance to CYSDV and acceptable yield by selecting or breeding plants having favorable alleles at the markers on chromosome 9 disclosed herein.

I. GENOMIC REGIONS, ALLELES, AND POLYMORPHISMS ASSOCIATED WITH CYSDV TOLERANCE IN MELON PLANTS

The invention provides novel introgressions of one or more alleles associated with disease tolerance and fruit yield in melon plants, together with polymorphic nucleic acids and linked markers for tracking the introgressions during plant breeding.

CYSDV can cause severe reduction in fruit quality and yield in a melon crop. Intensive efforts have therefore been made to identify effective sources of CYSDV tolerance. However, previously known introgressions from wild species have been associated with insufficient levels of tolerance or unacceptable associated deleterious traits. In particular, cultivated melon lines carrying previously known introgressions of CYSDV tolerance genes at the described chromosome 9 locus exhibit larger fruit size and reduced fruit set. These larger introgressions may be used to confer some CYSDV tolerance if used in a melon genetic background that effectively masks any associated unacceptable phenotypes but will not be acceptable across a broad range of melon types. The markers described here that are associated with CYSDV tolerance will also be useful for MAS of these larger introgressions. Despite many years of selective breeding in an effort to reduce the incidence of these unfavorable traits associated with CYSDV tolerance on chromosome 9, these effects are still routinely observed in the field. Examples of melon lines carrying introgressions conferring CYSDV tolerance are melon hybrid SV5133MG described in U.S. Patent Application No. 62/062,491, filed Oct. 10, 2014, and melon hybrid SV5845MP described in U.S. Patent Application No. 62/062,501, filed Oct. 10, 2014, each of which is incorporated herein by reference.

Melon lines exhibiting CYSDV tolerance, for example SV3218MG, McLaren, and SV3228MG, are known in the art and may be used in accordance with certain embodiments of the invention. Other CYSDV tolerance sources have also been described and are known in the art. For example, melon accession TGR-1551 (PI 482420) expressed tolerance to a Spanish strain of CYSDV (López-Sesé and Gómez-Guillamón, HortScience, 2000 35:1 pp. 110-113). Introduction (PI) 313970, described in EP1962578 B1, expressed high-level tolerance to CYSDV at Imperial Valley, Calif. and Yuma, Ariz. in 2006 and 2007 (McCreight and Wintermantel, Cucurbitaceae 2008, Proceedings of the IXth EUCARPIA Meeting (Pitrat M, ed). Additional, potential sources of tolerance to CYSDV include Ames 20203, PI 614185, and PI 614213 (McCreight and Wintermantel, 2008). Methods, tools and compositions associated with another CYSDV tolerance locus have been described in "Closterovirus-resistant melon plants" (EP1962578B1).

Using the improved genetic markers and assays of the invention, Applicants were able to successfully identify a novel CYSDV tolerance region associated with fewer deleterious traits when introgressed into a cultivated line. In certain embodiments, the invention provides melon plants comprising donor DNA from a CYSDV tolerant line between approximately 148.44 cM and 153.0 cM on chromosome 9 on consensus map v. 2.2.2. In other embodiments, the invention provides plants comprising introgressions located between approximately 149.93 cM and 150.7 cM on chromosome 9, or between approximately 149.93 cM and 150.36 cM on chromosome 9. These novel introgressions provide robust tolerance to CYSDV, while avoiding the reduction in fruit set and yield seen with conventional introgressions.

The invention further identifies and provides genomic segments on chromosome 9 flanked by marker locus NU0218332 and marker locus NU0219432, or by marker locus NCMEL008710187 and marker locus NCMEL008710191, or by marker locus NCMEL008710187 and marker locus NCMEL009432571, associated with CYSDV tolerance, but not associated with reduced fruit set or yield when introgressed into cultivated melon lines.

In particular embodiments, the invention provides a plant comprising donor DNA from a CYSDV tolerant plant at one or more of markers NU0220874, NU0219432, NU0218332, NU0243519, NCMEL009102569, NCMEL008710187, NCMEL008710191, and NCMEL009432571, which confers tolerance to CYSDV and does not exhibit reduced fruit set or yield.

In other embodiments, the invention provides a plant comprising a recombined introgression on chromosome 9 comprising a first allele conferring improved tolerance to CYSDV relative to a plant lacking said first allele, wherein said plant is homozygous for said recombinant introgression. In yet further embodiments, the invention provides a plant comprising a recombined introgression on chromosome 9 comprising a first allele conferring improved tolerance to CYSDV relative to a plant lacking said first allele, wherein said plant does not exhibit reduced fruit set or yield compared to a plant lacking said first allele. The recombined introgression may be deployed heterozygously or homozygously.

In another embodiment, the invention provides novel markers that may be used to identify a locus described herein, such as the markers set forth in FIGS. 1-3 and 5-7. Other embodiments of the invention provide novel markers NCMEL009102569, NCMEL008710187, NCMEL008710191, and NCMEL009432571 which have been shown to be genetically linked to CYSDV tolerance in melon plants.

II. INTROGRESSION OF GENOMIC REGIONS ASSOCIATED WITH DISEASE TOLERANCE

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a CYSDV tolerant plant into a cultivated line. The invention further provides markers for identifying and tracking the novel introgressions disclosed herein during plant breeding, including the markers set forth in FIGS. 1-3 and 5-7. Other embodiments of the invention provide novel markers NCMEL009102569, NCMEL008710187, NCMEL008710191, and NCMEL009432571, which have been shown to be genetically linked to CYSDV tolerance in plants.

Markers within or linked to any of the genomic intervals of the present invention may be useful in a variety of breeding efforts that include introgression of genomic regions associated with disease tolerance into a desired genetic background. For example, a marker within 40 cM, 20 cM, 15 cM, 10 cM, 5 cM, 2 cM, or 1 cM of a marker associated with disease tolerance described herein can be used for marker-assisted introgression of genomic regions associated with a disease tolerant phenotype.

Melon plants comprising one or more introgressed regions associated with a desired phenotype wherein at least 10%, 25%, 50%, 75%, 90%, or 99% of the remaining genomic sequences carry markers characteristic of the germplasm are also provided. Melon plants comprising an introgressed region comprising regions closely linked to or adjacent to the genomic regions and markers provided herein and associated with a disease tolerance phenotype are also provided.

III. DEVELOPMENT OF DISEASE TOLERANT MELON VARIETIES

For most breeding objectives, commercial breeders work within germplasm that is "cultivated," "cultivated type," or "elite." This germplasm is easier to breed because it generally performs well when evaluated for horticultural performance. A number of cultivated melon types have been developed, including Amarillo (AMA), Honeydew Green (HDG), Western Shipper (WSH), and Galia (GAL), which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach generally presents significant difficulties due to fertility problems associated with crosses between diverse lines, and negative linkage drag from the non-cultivated parent. For example, non-cultivated melon types can provide alleles associated with disease tolerance. However, these non-cultivated types may have poor horticultural qualities such as poor fruit quality, fruit set, or yield.

The process of introgressing desirable tolerance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease tolerance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease tolerance disclosed herein can be introgressed from one genotype to another and tracked using MAS. Thus, Applicants' discovery of accurate markers associated with disease tolerance will facilitate the development of melon plants having beneficial phenotypes. For example, seed can be genotyped using the markers of the present invention in order to select for plants comprising desired genomic regions associated with disease tolerance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore, in the absence of accurate markers, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among melon species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. MOLECULAR ASSISTED BREEDING TECHNIQUES

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics*, 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a melon plant a genotype associated with disease tolerance, identify a melon plant with a genotype associated with disease tolerance, and to select a melon plant with a genotype associated with disease tolerance. In certain embodiments of methods of the invention, polymorphic nucleic acids can be used to produce a melon plant that comprises in its genome an introgressed locus associated with disease tolerance. In certain embodiments of the invention, polymorphic nucleic acids can be used to breed progeny melon plants comprising a locus or loci associated with disease tolerance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease tolerance in melon plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996, 476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. DEFINITIONS

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which melon plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of melon breeding. An "elite population" is an assortment of elite individuals or varieties that can be used to represent the state of the art in terms of agronomically superior genotypes of a given crop species, such as melon. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to CYSDV.

As used herein, "tolerance allele" means the nucleic acid sequence associated with tolerance or resistance to disease.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. DEPOSIT INFORMATION

A deposit of melon hybrid SV5133MG and the inbred parent lines thereof, GALHK12-0024MO and GALHK12-0044AN, disclosed above and recited in the claims, has been made with the American Type Culture Collection (ATCC), 10801 University Blvd., Manassas, Va. 20110-2209. The date of the deposit was Sep. 30, 2014. The accession numbers for those deposited seeds of melon hybrid SV5133MG and inbred parent lines GALHK12-0024MO and GALHK12-0044AN are ATCC Accession Number PTA-121630, ATCC Accession Number PTA-121632, and ATCC Accession Number PTA-121633, respectively. A deposit of melon hybrid SV5845MP, and the inbred parent lines thereof, SPAHK11-0054AN and SPAHK11-0072AN, disclosed above and recited in the claims, has also been made with the American Type Culture Collection (ATCC), 10801 University Blvd., Manassas, Va. 20110-2209. The date of the deposit was Sep. 30, 2014. The accession numbers for those deposited seeds of melon hybrid SV5845MP and inbred parent lines SPAHK11-0054AN and SPAHK11-0072AN are ATCC Accession Number PTA- 121629, ATCC Accession Number PTA-121626, and ATCC Accession Number PTA-121627, respectively.

Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

EXAMPLES

Example 1

Fine-Mapping of CYSDV QTL9

A trial was conducted to fine-map the region conferring CYSDV tolerance on chromosome 9, which is present in the CYSDV-tolerant line GAL-188-CYSDV-DONOR. GAL-188-CYSDV-DONOR carries the full donor introgression in the 2-LOD QTL interval (NU0218332 to NU0243519, which corresponds to 148.44-157.87 cM) and flanking regions. BC1-derived lines from the cross of GA35PMT (3E_GA35PMT:1.12.9.11.10.999.15.@.99.3.) to GAL-188-CYSDV-donor and lines that carried recombination events in this genomic region were tested under virus pressure in greenhouse conditions. The plants were scored for CYSDV tolerance on a 1-9 scale at a first scoring date, and a second scoring date 22 days later (noted on FIG. 1 as scoring 1 and scoring 2, respectively). Plants were scored as follows: 1=no symptoms; 3=interveinal mottle and some yellow spots at the edges of bottom leaves; 5=obvious yellowing in bottom leaves; 7=obvious yellowing in bottom and intermediate leaves of plant might occur; 9=plant with general yellowing in the entire plant. The trial was arranged in a randomized complete block design (RCBD) with 5 replications. Each plot consisted of 4 plants transplanted into 4 different pots in the greenhouse, but quite frequently a plot had only 2 or 3 plants due to lack of seed and poor germination. Three lines served as controls, one carrying the full introgression in homozygous state, one carrying the full introgression in heterozygous state, and one lacking the full introgression. Two replicates from the same source seed of each of the three controls were included in the trial as distinct entries (noted in FIG. 1 as A1, A2, B1, B2, C1, and C2) to achieve higher replication and increase precision of least square means estimates. Entries with more than one letter in FIG. 1 correspond to recombinant bins that were bulked to obtain sufficient seed for testing.

Least square means (LSMeans) were estimated using a mixed model in JMP (SAS Institute, Inc., Cary, N.C.) for each of the scoring dates (FIG. 1). Mean separation groupings (MSG) and all pairwise differences among entries were also estimated. As also observed in the greenhouse, the second scoring showed more pronounced virus symptoms and allowed for better discrimination between susceptible and tolerant lines. Significant differences (a=0.05) were observed for the susceptible control replicates, although the source seed was the same for each of the two entries. In previous mapping studies, the disease scores of plants having the homozygous unfavorable genotype and the heterozygous genotype were estimated as 6.2 and 5.1, respectively, whereas plants having the homozygous favorable genotype had a disease score of 1.8. The additive effect of the QTL was estimated as 2a=−4.32 ($R^2$=0.84). The least square means of this experiment were consistent with previous estimates. The entries T, V, W, Y, Z, AA and ABAC did not provide significantly different phenotypes, as expected, so they could not provide any further insight for fine-mapping.

However, entries F, H, I, L, M, and NO showed a clear pattern of tolerant and susceptible phenotypes. Entries F, H, and I were significantly different from entries L, M, and NO. The data provided in FIG. 1 demonstrate that the CYSDV QTL on LG9 is located between the markers NU0220874 and NU0219432 in the interval of 146.9 cM to 153.0 cM. Since the 2-LOD interval of the QTL extends from NU0218332 to NU0243519, the QTL is most likely confined to the genomic region between NU0218332 and NU0219432 (148.44 cM to 153.0 cM) (FIG. 2).

Example 2

Additional Fine-Mapping of CYSDV QTL9 to the Interval Between 148.4 cM and 153.0 cM A second fine-mapping trial was conducted in order to further confirm that the CYSDV QTL9 region is localized to the interval between 148.4 cM and 153.0 cM. This second fine-mapping trial consisted of BC2F3s fixed for short donor introgressions in a recurrent parent background and was arranged in an RCBD design with 4 replications (FIG. 2). Two pairs of isogenic lines that carried the donor or recurrent parent allele at the QTL9 region were used as controls. Six plants were phenotyped for CYSDV in each replication for each experiment entry and a disease score was assigned using the 1-9 scale. The mean disease index was calculated and least square means were estimated using the appropriate mixed model in JMP. Necrotic symptoms were rarely observed in this trial, however, some extreme outliers were identified.

Results showed that significant differences were identified among control lines and experiment entries (FIG. 2). The entries 10, 8, 4 and 1 were significantly more disease tolerant than the entries 5, 6 and 2, which verifies that the CYSDV QTL9 is located in the interval between 148.4 cM and 153.0 cM (since the first marker shown in FIG. 1 is a flanking marker and the 2-LOD interval of the QTL starts at 148.4 cM).

Example 3

MABC Conversion of GAL Melons with the CYSDV QTL9 Introgression

A converted line comprising the introgression of the CYSDV QTL9 allele derived from the donor line GAL-188-CYSDV-DONOR was developed using marker-assisted backcrossing (MABC), and the resulting phenotypes were evaluated. The inbred line converted was GAL-188-DUFFE-AN, the female parent of the hybrid DRG3261. BC2 seed of this converted inbred was obtained, and the CYSDV QTL9 introgression was fixed for the homozygous donor and recurrent parent alleles. The resulting lines were trialed next to the line carrying the heterozygous introgression and the unconverted inbred line. The approximate percentage of recurrent parent genome for this BC2-derived conversion was 82.69% and the donor introgression at CYSDV QTL9 spanned at least the region of 146.91 cM to 168.08 cM (a minimum of 21.17 cM). These BC2-derived conversions were tested for CYSDV efficacy in a greenhouse assay. Lines with and without the donor introgression were phenotyped in an RCBD trial with 4 replications and 5 plants per replication. Lines with the donor introgression at CYSDV QTL9 were scored as completely tolerant (Least Square Mean (LSM)=1.0) while lines with recurrent patent allele at this locus were scored as susceptible (LSM=9.0).

The trial was arranged in an RCBD design with 5 replications. Five fruits were collected from each of the 10-plant plots and were phenotyped for rind and flesh color traits using a handheld colorimeter at field maturity. Two additional melons were harvested from each plot and were transferred to the cold storage (4° C.). One of these two fruits was phenotyped for rind and flesh color traits 24 days after harvest and the second 35 days after harvest. In addition to color traits, phenotypes for several other melon traits were recorded at field maturity. Least square mean estimates, mean separation groupings, differences among genotypes for various traits, and relevant statistics within and across time points (field, 24 days after storage, and 35 days after storage) were estimated.

Phenotypes at field maturity indicated statistically significant differences for fruit size (length and width) and fruit set associated with the large donor introgression at CYSDV QTL9. Lines with homozygous donor introgressions had larger width (5.36-8.98 mm), larger length (8.76-13.16 mm), and reduced fruit set (4.6-11.6 fruit/plot) (Table 1). Therefore, loci affecting fruit size and fruit set appear to be localized in proximity with the CYSDV QTL9 locus.

Differences in the color of the foliage were also observed in the trial. Lines that carried the homozygous donor introgression had much deeper green leaf color and could be easily distinguished from the rest of the entries in the trial at the time of fruit field maturity, but not in earlier stages of plant development.

Table 1.

Phenotypes of homozygous donor (DN), homozygous recurrent parent (RP), heterozygous (HET) introgressions next to the unconverted inbred lines (FS) for the GAL-188-DUFFE-AN MABC conversion carrying the CYSDV QTL9. Significant differences in fruit length, fruit width, and fruit set were observed. Least square means (LSM) and mean significant group (MSG) differences are shown.

| Entry | Length (mm) | | Width (mm) | | Fruit Set (# fruits/plot) | |
|---|---|---|---|---|---|---|
| | LSM | MSG | LSM | MSG | LSM | MSG |
| DN | 132.3 | A | 131.4 | A | 46.4 | C |
| HET | 129.2 | A | 129.2 | BA | 53.4 | BA |
| RP | 120.5 | B | 122.5 | C | 58.0 | A |
| FS | 119.1 | B | 126.1 | BC | 56.4 | BA |

Example 4

Fine-Mapping of CYSDV QTL9 to a 0.77 cM Interval

CYSDV QTL9 was previously fine-mapped to the interval of 148.4 cM to 153.0 cM. This interval includes a large number of genes including the SGR gene, a homolog to the chlorophyll-retainer mutant in pepper.

In order to further refine the interval associated with disease tolerance, several recombination events were identified in the CYSDV QTL9 interval in a BC2-derived population in a GAL background derived from the cross of GA35PMT×GAL-188-CYSDV-DONOR. Lines were phenotyped under whitefly pressure over three different seasons with five replications using randomized designs and were also genotyped with markers across the fine-mapped interval. Marker density in this CYSDV QTL9 genomic region was increased using newly identified SNPs. In addition, a novel SNP marker was developed through re-sequencing within the coding sequence of the SGR gene (NC-MEL009102569). This SNP is actually a putative genetic variant leading to an amino acid change in a region of the SGR protein that is conserved among diverse plant species. Point mutations leading to single amino acid changes in this region were found to result in stay-green phenotypes in tomato and pepper.

Due to the significant effect of this locus, phenotypic data allowed the identification of a susceptible or tolerant phenotype for each line, and therefore data are presented across locations (FIG. 3). The data indicate that the CYSDV QTL9 locus is in the interval of NCMEL008710187 to NCMEL008710191 (149.93 cM to 150.70 cM) spanning a 0.77 cM region which includes NCMEL009102569 (FIG. 3). Four candidate genes are included within the 0.77 cM interval. Two have unknown functions, one is a MADS-box transcription factor likely implicated in flowering and plant development processes (with two putative transcripts), and last is the SGR gene. Order and location of these genes on the physical map is shown in Table 2.

TABLE 2

List of genes within the 0.77 cM interval of CYSDV QTL9. The description based on annotation and position in the physical assembly is shown.

| Gene description | Physical position (bp) |
|---|---|
| Chlorophyll retainer (SGR gene) | 20171949-20174371 |
| MADS box transcription factor | 20181215-20185105 |
| Isoform 2 of Protein FAM63A | 20191228-20198138 |
| hypothetical protein | 20198262-20200852 |

Galia (GAL) melons typically exhibit a green flesh when harvested at field maturity, but flesh turns white after storage. The stay-green phenotype in the flesh of fruit from the BC2-derived lines was evaluated in a randomized design with five replications. Flesh color was measured using a handheld colorimeter at the time of maturity in the field from 5 melons. Three melons were harvested and kept in cold storage for 5-6 weeks. Flesh color of the stored melons was measured 22-25 days and 36-40 days after storage. Lines carrying the donor allele at the SGR gene showed no significant change in chroma or hue after cold storage (FIG. 4, bottom panels). However, for lines carrying the GAL recurrent parent alleles at the SGR gene, as well as three GAL hybrids used as color controls, chroma and hue decreased significantly after 36-40 days of cold storage (FIG. 4, top panels).

Example 5

Re-Sequencing of the 0.77 cM Interval Comprising CYSDV QTL9

These results show that the CYSDV QTL9 co-segregates with the SGR gene. The GAL-188-CYSDV-DONOR allele at this locus may be responsible for the lack of change in flesh color in GAL melons after cold storage, and various other stay-green phenotypes on foliage, fruit rind, and fruit flesh of melons across market types. It therefore appears that a rare allele within or genetically linked to the SGR gene may pleiotropically affect disease tolerance phenotypes. However, the 0.77 cM region identified harbors four candidate genes and no additional polymorphic markers had been identified within this genomic region previously. In order to identify additional SNPs for refining the genomic interval, the identified 0.77 cM interval comprising CYSDV QTL9 was re-sequenced, focusing primarily on the four coding sequences in the two parents of the CYSDV mapping population, GAL-188-CYSDV-DONOR and GA35PMT.

Approximately 81% of the 0.77 cM interval was re-sequenced. A novel SNP was identified, which was located between the MADS box and FAM63A genes at 20,187,669 bp. The SNP was converted to the TaqMan marker NCMEL009432571. The BC2-derived lines from the cross of GA35PMT×GAL-188-CYSDV-DONOR that carried recombination events at the target genomic region, and which had previously been phenotyped in replicated trials under CYSDV infection, were genotyped using this new marker.

Figure 5:
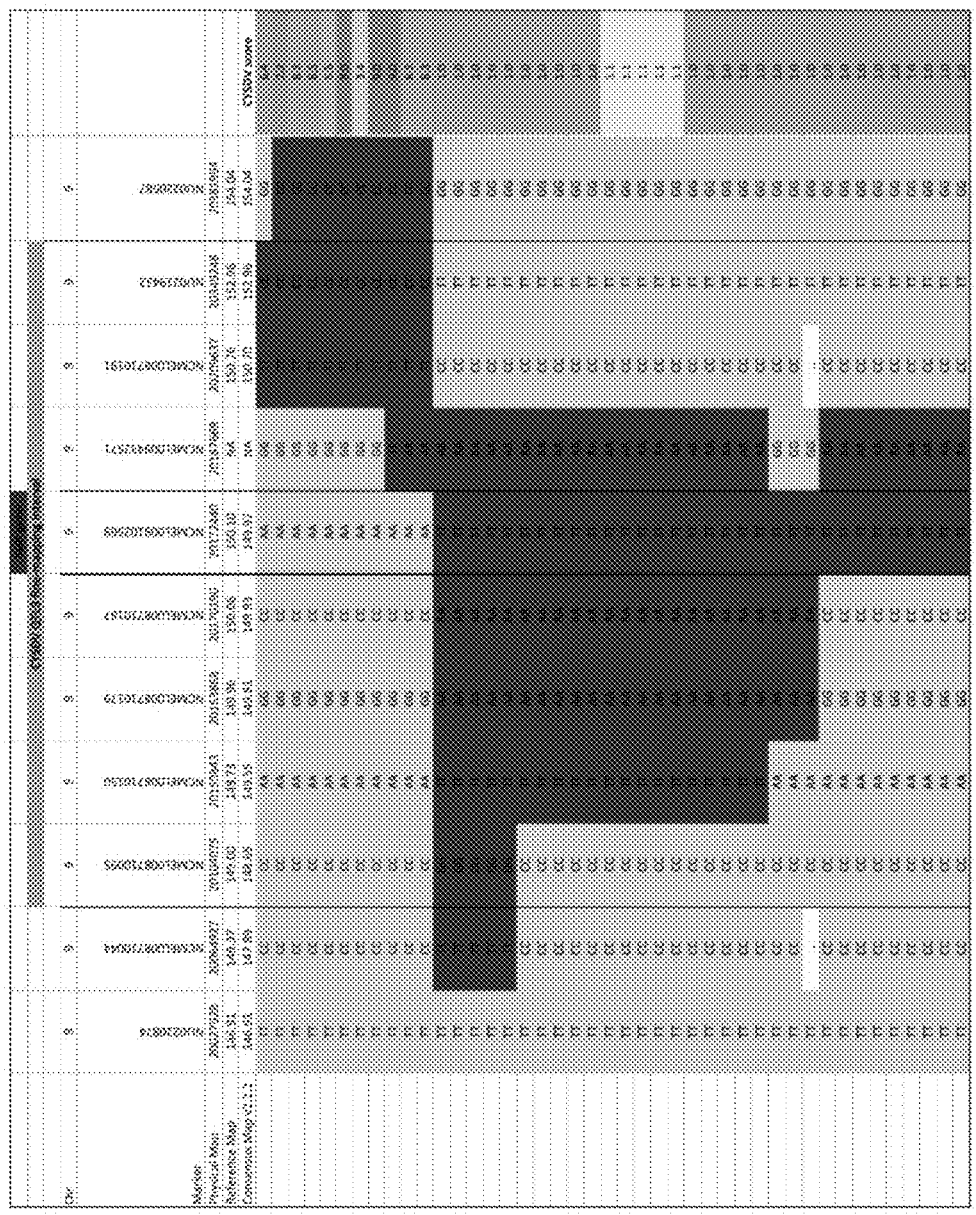
FIG. 5: Shows disease phenotypes and donor introgressions of the BC2-derived lines carrying recombination events in the identified CYSDV QTL interval. CYSDV tolerance scores were evaluated on a 1-9 scale and are reported as least square means. Data reported are from multiple trialing seasons. Alleles from the GAL-188-CYSDV-DONOR are shown in gray and alleles from the susceptible recurrent parent GA35PMT are shown in white.

Results showed that the genetic factor conferring CYSDV tolerance is located within the interval of NCMEL008710187 to NCMEL009432571, which is 17,479 bp in length and is expected to span a ~0.07 cM genetic interval (FIG. 5). This interval harbors only the SGR gene and the MADS-box transcription factor. The latter is unlikely to be implicated in a disease tolerance phenotype based on current reports of its function in different plant species. Therefore, these results suggest that the CYSDV QTL9 co-segregates with the SGR gene, in agreement with the hypothesis that a rare allele within or genetically linked to the SGR gene in GAL-188-CYSDV-DONOR pleiotropically affects disease phenotypes (FIG. 5).

Example 6

Development of Informative Markers for MAS

After extensive re-sequencing in the interval between markers NCMEL008710187 and NCMEL009432571, which is associated with CYSDV tolerance, a novel SNP (NCMEL009102569) was identified between the parents GAL-188-CYSDV-DONOR and GA35PMT. Marker NCMEL009102569 was used to analyze 70 diverse susceptible lines from different MCT and 11 tolerant lines (Table 3). The marker genotype was highly associated with the phenotype (Table 4), indicating that this marker can be used to track introgression of the CYSDV QTL from a line carrying the QTL into a wide range of susceptible lines from different melon market types. Thus, the marker NCMEL009102569 is very useful for MAS or MABC.

TABLE 3

Genotypic and phenotypic data in susceptible and tolerant lines.

| Line No. | MCT | Phenotype | NCMEL009102569 |
|---|---|---|---|
| 1 | AMA | R | TT |
| 2 | AMA | R | TT |
| 3 | AMA | R | TT |
| 4 | GAL | R | TT |
| 5 | GAL | R | TT |
| 6 | GAL | R | TT |
| 7 | GAL | R | TT |
| 8 | GAL | R | TT |
| 9 | KIR | R | AA |
| 10 | SPA | R | TT |
| 11 | SPA | R | TT |
| 12 | AMA | IR | AA |
| 13 | AMA | IR | AA |
| 14 | ANA | IR | AA |
| 15 | ANA | IR | AA |

TABLE 3-continued

Genotypic and phenotypic data in susceptible and tolerant lines.

| Line No. | MCT | Phenotype | NCMEL009102569 |
|---|---|---|---|
| 16 | CHA | IR | AA |
| 17 | WSH | IR | AA |
| 18 | GAL | S | AA |
| 19 | GAL | S | AA |
| 20 | AMA | S | AA |
| 21 | AMA | S | AA |
| 22 | AMA | S | AA |
| 23 | AMA | S | AA |
| 24 | AMA | S | AA |
| 25 | AMA | S | AA |
| 26 | AMA | S | AA |
| 27 | AMA | S | AA |
| 28 | AMA | S | AA |
| 29 | AMA | S | AA |
| 30 | AMA | S | AA |
| 31 | AMA | S | AA |
| 32 | AMA | S | AA |
| 33 | AMA | S | AA |
| 34 | AMA | S | AA |
| 35 | AMA | S | AA |
| 36 | AMA | S | AA |
| 37 | AMA | S | AA |
| 38 | AMA | S | AA |
| 39 | ANA | S | AA |
| 40 | ANA | S | AA |
| 41 | ANA | S | AA |
| 42 | ANA | S | AA |
| 43 | ANA | S | AA |
| 44 | ANA | S | AA |
| 45 | ANA | S | AA |
| 46 | ANA | S | AA |
| 47 | ANA | S | AA |
| 48 | ANA | S | AA |
| 49 | ANA | S | AA |
| 50 | ANA | S | AA |
| 51 | ANA | S | AA |
| 52 | ANA | S | AA |
| 53 | CHA | S | AA |
| 54 | CHA | S | AA |
| 55 |  | S | AA |
| 56 |  | S | AA |
| 57 | GAL | S | AA |
| 58 | GAL | S | AA |
| 59 | GAL | S | AA |
| 60 | GAL | S | AA |
| 61 | GAL | S | AA |
| 62 | GAL | S | AA |
| 63 | GAL | S | AA |
| 64 | GAL | S | AA |
| 65 | GAL | S | AA |
| 66 | GAL | S | AA |
| 67 | GAL | S | AA |
| 68 | GAL | S | AA |
| 69 | GAL | S | AA |
| 70 | GAL | S | AA |
| 71 | GAL | S | AA |
| 72 | GAL | S | AA |
| 73 | GAL | S | AA |
| 74 | GAL | S | AA |
| 75 | GAL | S | AA |
| 76 | SPA | S | AA |
| 77 | SPA | S | AA |
| 78 | SPA | S | AA |
| 79 | SPA | S | AA |
| 80 | SPA | S | AA |
| 81 | SPA | S | AA |
| 82 | SPA | S | AA |
| 83 | SPA | S | AA |
| 84 | SPA | S | AA |
| 85 | SPA | S | AA |
| 86 | SPA | S | AA |
| 87 | SPA | S | AA |
| 88 | SPA | S | AA |
| 89 | SPA | S | AA |
| 90 | SPA | S | AA |
| 91 | SPA | S | AA |

TABLE 3-continued

Genotypic and phenotypic data in susceptible and tolerant lines.

| Line No. | MCT | Phenotype | NCMEL009102569 |
|---|---|---|---|
| 92 | SPA | S | AA |
| 93 |  | S | AA |
| 94 | GAL | S | AA |
| 95 | WSH | S | AA |
| 96 | WSH | S | AA |

AMA = Amarillo; ANA = Ananas; CHA = Charentais; GAL = Galia; KIR = Kirkagac; SPA = Spanish/Piel de Sapo; WSH = Western Shipper.

TABLE 4

Favorable allele frequency at marker NCMEL009102569 in tolerant and susceptible groups.

| V2.2.2 | Consensus Map Chr | 9 |
|---|---|---|
|  | Consensus Map Position | 150 |
|  | Market | NCMEL009102569 |
|  | Favorable Allele | TT |

| Phenotypic Group | N | | |
|---|---|---|---|
| R | 11 | Favorable Allele Frequency | 0.91 |
| S | 79 | Favorable Allele Frequency | 0.00 |

Example 7

Development of Efficacious Breeding Events

Two lines that carry small donor introgressions conferring CYSDV tolerance were identified in GAL (white flesh) and WSH (orange flesh) backgrounds to facilitate the deployment of this locus through MAS or MABC. The need for these lines was evident after testing of early GAL MABC conversions carrying large donor introgressions at the genomic region around approximately 21.2 cM. These larger introgressions resulted in undesirable phenotypes such as larger fruit size and lower fruit set. GALZA13-0008AN is a BC2F5 line with 87.81% recurrent parent (GA35PMT) and 0.06% remnant heterozygosity. WSHZA13-0009AN is a BC2F4 line with 87.11% recurrent parent (WSH-39-1067-AN) and 4.52% remnant heterozygosity. These BC2-derived lines were selected based on recombination events in the genomic region surrounding the SGR gene and carrying GAL-188-CYSDV-DONOR allele introgressions smaller than 0.7 cM. The SNP marker developed within the SGR gene, NCMEL009102569 (149.97 cM; 20,172,440 bp), which is highly informative across melon types, can be used to transfer these short introgressions into different breeding germplasm.

Phenotypic efficacy of the two lines has been confirmed. GALZA13-0008AN and WSHZA13-0009AN were found to be tolerant to CYSDV infection based on bioassay experiments (Table 5), and in previous generations during the development of the lines. Both lines carry the GAL-188-CYSDV-DONOR allele at marker NCMEL009102569 (FIG. 6), which is expected to be associated with tolerance to CYSDV infection.

TABLE 5

Phenotypic efficacy of breeding events. Lines were found to be CYSDV tolerant (least square mean 1.0-1.9 on a 1-9 scale) in two different trials.

| Pedigree | Location | Reps | # Plants Tested | LS Mean |
|---|---|---|---|---|
| GALZA13-0008AN | San Nicholas, Spain | 5 | 30 | 1.0 |
| WSHZA13-0009AN | San Nicholas, Spain | 5 | 13 | 1.0 |
| GALZA13-0008AN | El Ejido, Spain | 4 | 28 | 1.0 |
| WSHZA13-0009AN | El Ejido, Spain | 4 | 27 | 1.9 |

Example 8

Confirming Efficacy Across Market Types

Six inbred lines from four different market types, Amarillo (AMA), Honeydew Green (HDG), Western Shipper (WSH) and Galia (GAL), were converted with the GAL-188-CYSDV-DONOR allele at the CYSDV QTL9 genomic region through MABC. These lines are parents of four melon hybrids (Table 6). Hybrids were developed from crosses of BC3F3 lines derived through MABC. In two cases both parents of the hybrid carried donor introgressions at the CYSDV QTL9 locus, while for the rest of the hybrids only one parental line carried the donor introgression at the CYSDV QTL9 locus (Table 6). Markers at the CYSDV QTL9 locus that were informative for the respective crosses were used for genotypic selection of the GAL-188-CYSDV-DONOR haplotype at the BC1 and subsequent backcross generations, while at the same time background markers were used to select for the recurrent parent across the rest of the genome. This genotypic data was used to derive the percentage of the recurrent parent across the genome and the minimum and maximum size of the donor introgression at the CYSDV QTL9 locus (Table 6). Donor introgressions were also estimated using genotyping data and are shown in Table 6 (genetic positions in cM are from consensus map v. 2.2.2). In all cases the lines carry the CYSDV QTL9 fine-mapped region (149.93-150.70 cM).

Inbred MABC conversions, unconverted inbred lines, hybrids, and eight controls were phenotyped under CYSDV pressure in the greenhouse using whiteflies. The trial was planted in an RCBD with 5 replications and 6 plants per replication, and was scored on a scale of 1-9. Least square means and relevant statistics were obtained using JMP. Means for inbred MABC conversions and hybrids are shown on Table 6. All converted inbred lines scored as highly tolerant to CYSDV. Hybrids that carried the donor introgressions at the CYSDV QTL9 locus in both of their parent lines also scored as highly tolerant to CYSDV, while the rest of the hybrids (with only one parent line that carried the donor introgression at the CYSDV QTL9 locus) scored as susceptible to CYSDV. This latter result may be due to the very high disease pressure in the greenhouse and not due to the recessive gene action of this locus. These results demonstrate that the GAL-188-CYSDV-DONOR introgression can be transferred through genotypic selection into various genetic backgrounds across melon types and produce lines highly tolerant to CYSDV infection.

TABLE 6

Inbred lines from four melon market types converted using MABC. Size of the GAL-188-CYSDV-DONOR introgression at the CYSDV QTL9 locus and % recurrent parent across the genome for each MABC conversion are shown.

| Line No. | Market Type | % RP | Min Introgression Interval (cM) | Max Introgression Interval (cM) | Inbred Phenotypic Score | Donor Introgression in Hybrid | Hybrid Phenotypic Score |
|---|---|---|---|---|---|---|---|
| 1 | AMA | 98.65 | 149.2-157.9 | 146.9-158.7 | 1 | Hom | 1 |
| 2 | AMA | 98.57 | 135.5-154.0 | 117.6-162.4 | 1.1 | | |
| 3 | AMA | 98.65 | — | — | — | Het | 8.5 |
| 4 | AMA | 98.57 | 135.5-154.0 | 117.6-162.4 | 1.1 | | |
| 5 | HDG | 95.89 | 149.2-187.1 | 146.9-189.0 | 1 | Hom | 1 |
| 6 | HDG | 98.82 | 149.2-157.9 | 146.9-185.8 | 1 | | |
| 7 | HDG | 95.89 | — | — | — | Het | 8.3 |
| 8 | HDG | 98.82 | 149.2-157.9 | 146.9-158.7 | 1 | | |
| 9 | WSH | 96.81 | — | — | — | Het | 8 |
| 10 | WSH | 98.08 | 149.2-187.1 | 146.9-189.0 | 1 | | |
| 11 | GAL | 85.28 | — | — | — | Het | 4.6 |
| 12 | GAL | 97.93 | 149.2-157.9 | 146.9-158.7 | 1 | | |

Example 9

Evaluation of GAL Melons Comprising a Minimal CYSDV QTL9 Introgression

The lines carrying the breeding events, GALZA13-0008AN and WSHZA13-0009AN, were trialed in the field in Woodland, Calif. Lines comprising the small introgression were evaluated for the stay-green phenotype, and further evaluated for negative traits previously associated with the stay-green phenotype, including increased fruit size and reduced fruit set. The recurrent parents and the donor line GAL-188-CYSDV-DONOR were included in the trial with GALZA13-0008AN and WSHZA13-0009AN. The trial was arranged in an RCBD with seven replications. Fruits were harvested at field maturity and were evaluated for fruit size (length and width) and fruit set (fruit per plot). Fruit size and fruit set were evaluated as linkage drag observed with larger introgressions in a previous trial (Table 1).

Least square means and mean separation groupings were estimated for fruit size and fruit set (Table 7). The data showed that there was a significant difference in fruit length in both lines compared with their respective RP and a significant difference in fruit width in GALZA13-0008AN compared with its RP. The very small size of the introgression suggests that this difference in size is a background effect from the donor. Candidate genes in the introgression have been identified (Table 2) and there is no obvious link between those genes and fruit size. GALZA13-0008AN and WSHZA13-0009AN are BC2-derived and 87% RP (FIG. 6), therefore the presence of background effects is likely.

No significant difference in fruit set was detected between the lines carrying the breeding event and their respective RP. These data therefore show that the shorter introgression has eliminated the reduced fruit set that was seen in the lines with the larger introgression (Table 1).

Fruit rind and fruit flesh color changes associated with stay-green were also examined at field maturity, 21 days post harvest and 40 days post harvest. The data are consistent with previous trials and confirm that the short introgression is associated with the stay-green phenotype.

TABLE 7

Fruit size and fruit set in lines carrying introgressions from GAL-188-CYSDV-DONOR.

| Line Description | Pedigree | Fruit Width (mm) | | | Fruit Length (mm) | | | Fruit Set | | |
|---|---|---|---|---|---|---|---|---|---|---|
| | | LSM | SE | MSG | LSM | SE | MSG | LSM | SE | MSG |
| Galia Recurrent Parent | GA35PMT (RP) | 129.3 | 2.0 | E | 131.1 | 2.5 | DE | 45.9 | 2.2 | C |
| Event in Galia background | GALZA13-0008AN | 136.5 | 3.0 | CD | 147.2 | 3.8 | C | 46.7 | 2.2 | C |
| Western Shipper Recurrent Parent | WSH-39-1067-AN (RP) | 140.2 | 2.8 | BC | 164.0 | 3.5 | A | 26.9 | 2.2 | E |
| Event in Western Shipper background | WSHZA13-0009AN | 144.4 | 2.2 | B | 156.3 | 2.7 | B | 28.9 | 2.2 | E |
| Full length introgression, Galia background | GAL-188-CYSDV-DONOR | 117.3 | 2.3 | F | 114.5 | 2.9 | F | 55.9 | 2.2 | A |

Example 10

Markers for Marker-Assisted Selection During Breeding

Table 8 provides a summary of the marker loci identified and provided herein for identifying and tracking CYSDV tolerance alleles in plants. Table 8 further provides primer and probe sequences useful in assays during MAS or MABC in plant breeding, for example for use in TaqMan assays.

TABLE 8

Useful markers for selection of CYSDV tolerance alleles during plant breeding.

| Marker | Chr. | Pos. | Alleles | R Allele | S Allele | VIC Probe SEQ ID | FAM Probe SEQ ID | F Primer SEQ ID | R Primer SEQ ID |
| --- | --- | --- | --- | --- | --- | --- | --- | --- | --- |
| NU0220874 | 9 | 146.91 | A/T | A | T | 1 | 2 | 3 | 4 |
| NU0219432 | 9 | 152.96 | T/C | C | T | 5 | 6 | 7 | 8 |
| NU0218332 | 9 | 148.44 | A/C | A | C | 9 | 10 | 11 | 12 |
| NU0243519 | 9 | 157.88 | A/G | G | A | 13 | 14 | 15 | 16 |
| NCMEL009102569 | 9 | 150.1 | A/T | T | A | 17 | 18 | 19 | 20 |
| NCMEL008710187 | 9 | 150.06 | A/C | A | C | 21 | 22 | 23 | 24 |
| NCMEL008710191 | 9 | 150.76 | C/T | T | C | 25 | 26 | 27 | 28 |
| NCMEL009432571 | 9 | 150.36 | A/G | A | T | 29 | 30 | 31 | 32 |

Any of the foregoing markers may be used to recreate as well as select a further recombined introgression fragment lacking particular linked deleterious traits from the introgression donor genome, for example, from donor lines as detailed here. For example, selections may be made from melon hybrid SV5133MG and the inbred parent lines thereof, GALHK12-0024MO and GALHK12-0044AN, or melon hybrid SV5133MG and inbred parent lines GALHK12-0024MO and GALHK12-0044AN, or from a wild source of the trait, to obtain an introgression of reduced size lacking a deleterious trait linked to the introgressed segment in the donor. In addition, markers detailed in this application may be used to track the presence of any size introgression fragment in progeny of a cross with a donor containing a large introgression or smaller introgression fragment with reduced drag. For example, markers NU0218332 and NU0243519, or any markers or sets of markers that lie between them, may be used to assay for the presence of an allele associated with the desired CYSDV tolerance phenotype to assay for and select the presence of an introgression fragment in progeny of a cross.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A melon plant of a cultivated melon variety comprising a recombinant introgression on chromosome 9 from a donor melon plant having tolerance to cucurbit yellow stunt disorder virus, wherein said recombinant introgression comprises a first allele conferring improved tolerance to cucurbit yellow stunt disorder virus relative to a plant lacking said first allele, and wherein:
   (i) said plant is homozygous for said recombinant introgression; or
   (ii) said recombinant introgression lacks a second allele genetically linked to said first allele and conferring reduced fruit set or fruit yield compared to a plant lacking said second allele,
   wherein said first allele conferring improved tolerance to cucurbit yellow stunt disorder virus includes marker locus NCMEL009102569, and wherein said first allele is present in the genome of a melon plant selected from the group consisting of melon hybrid SV5133MG, melon inbred GALHK12-0024MO, melon inbred GALHK12-0044AN, melon hybrid SV5845MP, melon inbred SPAHK11-0054AN and melon inbred SPAHK11-0072AN; representative samples of seed of which have been deposited under ATCC Accession Numbers PTA-121630, PTA-121632, PTA-121633, PTA-121629, PTA-121626, and PTA-121627, respectively.

2. The melon plant of claim 1, wherein said recombinant introgression:
   (i) is within a genomic segment flanked by marker locus NU0218332 and marker locus NU0219432; or
   (ii) is located between approximately 148.44 cM and 153.0 cM on chromosome 9.

3. The melon plant of claim 1, wherein said recombinant introgression lacks a second allele genetically linked to said first allele and conferring reduced fruit set or fruit yield compared to a plant lacking said second allele and wherein said plant is heterozygous or homozygous for said recombinant introgression.

4. The melon plant of claim 1, wherein said recombinant introgression is within a genomic segment flanked by marker locus NCMEL008710187 and marker locus NCMEL008710191.

5. The melon plant of claim 4, wherein said recombinant introgression is within a genomic segment flanked by marker locus NCMEL008710187 and marker locus NCMEL009432571.

6. The melon plant of claim 5, wherein said recombinant introgression comprises marker locus NCMEL009102569.

7. The melon plant of claim 1, wherein said recombinant introgression is located between approximately 149.93 cM and 150.7 cM on chromosome 9.

8. The melon plant of claim 7, wherein said recombinant introgression is located between approximately 149.93 cM and 150.36 cM on chromosome 9.

9. The melon plant of claim 1, wherein said plant comprises DNA from said donor plant at marker locus NCMEL009102569 and recipient DNA at marker locus NCMEL008710191.

10. A plant part of the plant of claim 1.

11. The plant part of claim 10, wherein said plant part is a cell, a seed, a root, a stem, a leaf, a fruit, a flower, or pollen.

12. A method for producing a melon plant with improved tolerance to cucurbit yellow stunt disorder virus comprising:
   a) crossing the melon plant of claim 1 with itself or with a second melon plant of a different genotype to produce one or more progeny plants; and
   b) selecting a progeny plant comprising said recombinant introgression.

13. The method of claim 12, wherein selecting said progeny plant comprises identifying a progeny plant that: (1) comprises donor DNA at a locus genetically linked to said first allele and/or lacks an allele present at the corresponding locus in said melon plant; and (2) lacks donor DNA at a locus genetically linked to said second allele that confers increased fruit size or reduced fruit set, and/or comprises an allele present at the corresponding locus in said melon plant.

14. The method of claim 12, wherein selecting said progeny plant comprises marker-assisted selection (MAS).

15. The method of claim 14, wherein marker-assisted selection (MAS) comprises detecting at least one allele at a marker locus selected from the group consisting of: NU0220874, NU0219432, NU0218332, NU0243519, NCMEL009102569, NCMEL008710187, NCMEL008710191, and NCMEL009432571.

16. The method of claim 15, wherein marker-assisted selection (MAS) comprises detecting at least one allele at a marker locus selected from the group consisting of: NCMEL009102569, NCMEL008710187, NCMEL008710191, and NCMEL009432571.

17. The method of claim 16, wherein marker-assisted selection (MAS) comprises detecting at least one allele at marker locus NCMEL009102569.

18. The method of claim 12, wherein said progeny plant is an F2-F6 progeny plant; or wherein producing said progeny plant comprises backcrossing.

19. The method of claim 18, wherein backcrossing comprises from 2-7 generations of backcrossing.

20. A method for obtaining a melon plant exhibiting improved tolerance to cucurbit yellow stunt disorder virus comprising:
    a) obtaining a melon plant heterozygous for a first allele that confers tolerance to cucurbit yellow stunt disorder virus and that is genetically linked in the plant to a second allele that confers increased fruit size or reduced fruit set;
    (b) obtaining progeny of the plant; and
    (c) selecting at least a first progeny plant in which recombination has occurred such that the progeny comprises said first allele that confers tolerance to cucurbit yellow stunt disorder virus but not said second allele that confers increased fruit size or reduced fruit set;
    wherein selecting said first progeny plant comprises detecting at least one allele at a locus selected from the group consisting of: NU0220874, NU0219432, NU0218332, NU0243519, NCMEL009102569, NCMEL008710187, NCMEL008710191, and NCMEL009432571.

21. The method of claim 20, wherein said progeny plant is an F2-F6 progeny plant; or wherein producing said progeny plant comprises backcrossing.

22. The method of claim 21, wherein backcrossing comprises from 2-7 generations of backcrossing.

23. A plant produced by the method of claim 20, wherein the plant comprises said first allele that confers tolerance to cucurbit yellow stunt disordervirus and not said second allele that confers increased fruit size or reduced fruit set, and wherein the allele that confers tolerance to cucurbit yellow stunt disorder virus includes marker locus NCMEL009102569 and is present in the genome of a melon plant selected from the group consisting of melon hybrid SV5133MG, melon inbred GALHK12-0024MO, melon inbred GALHK12-0044AN, melon hybrid SV5845MP, melon inbred SPAHK11-0054AN and melon inbred SPAHK11-0072AN; representative samples of seed which have been deposited under ATCC Accession Numbers PTA-121630, PTA-121632, PTA-121633, PTA-121629, PTA-121626, and PTA-121627, respectively.

24. A part of the plant of claim 23, selected from the group consisting of a cell, a seed, a root, a stem, a leaf, a fruit, a flower, and pollen.

25. A melon plant of a cultivated melon variety comprising a recombinant introgression on chromosome 9 conferring improved tolerance to cucurbit yellow stunt disorder, wherein said recombinant introgression comprises the recombinant introgression found at marker locus NCMEL009102569 in melon hybrid SV5133MG, melon inbred GALHK12-0024MO, melon inbred GALHK12-0044AN, melon hybrid SV5845MP, melon inbred SPAHK11-0054AN or melon inbred SPAHK11-0072AN; wherein a representative sample of seed of said plants has been deposited under ATCC Accession Numbers PTA-121630, PTA-121632, PTA-121633, PTA-121629, PTA-121626, and PTA-121627, respectively.

* * * * *